United States Patent [19]

Boehmer et al.

[11] Patent Number: 5,269,763
[45] Date of Patent: Dec. 14, 1993

[54] SELF-SEALING CANNULA CAP

[75] Inventors: Dennis A. Boehmer, Xenia; Gerardus M. Stello, Yellow Springs, both of Ohio

[73] Assignee: Vernay Laboratories, Inc., Yellow Springs, Ohio

[21] Appl. No.: 732,143

[22] Filed: Jul. 18, 1991

[51] Int. Cl.⁵ .............................................. A61M 5/00
[52] U.S. Cl. .................................. 604/167; 604/169; 604/256; 251/149.1
[58] Field of Search ............... 604/164, 167, 169, 256, 604/905; 251/149.1; 137/843, 849

[56] References Cited

U.S. PATENT DOCUMENTS

| | | | |
|---|---|---|---|
| 4,000,739 | 1/1977 | Stevens | 604/167 |
| 4,096,860 | 6/1978 | McLaughlin | 604/167 |
| 4,436,519 | 3/1984 | O'Neill | 604/256 |
| 4,626,245 | 12/1986 | Weinstein | 604/167 |
| 4,655,752 | 4/1987 | Honkanen et al. | 604/167 |
| 4,673,393 | 6/1987 | Suzuki et al. | 604/167 |
| 4,798,594 | 1/1989 | Hillstead | 604/167 |
| 4,857,062 | 8/1989 | Russell | 604/256 |
| 4,895,565 | 1/1990 | Hillstead | 604/167 |
| 4,909,798 | 3/1990 | Fleishhacker et al. | 604/256 |
| 4,917,668 | 4/1990 | Haindl | 604/167 |
| 4,924,923 | 5/1990 | Boehmer et al. | 141/312 |
| 4,929,235 | 5/1990 | Merry et al. | 604/256 |
| 4,948,092 | 8/1990 | Kasper et al. | 251/82 |
| 4,954,149 | 9/1990 | Fullemann | 55/386 |
| 4,960,412 | 10/1990 | Fink | 604/256 |

*Primary Examiner*—John J. Wilson
*Attorney, Agent, or Firm*—Biebel & French

[57] ABSTRACT

A cap is provided for resealably sealing the end of a cannula to allow the insertion and removal of a tube or surgical instrument such as a needle into the cannula. The cap includes a valve body having a plurality of radially extending lip members arranged to form a pair of intersecting duckbill valves and a sleeve is provided for mounting the cap member to the end of a cannula.

14 Claims, 4 Drawing Sheets

SELF-SEALING CANNULA CAP

BACKGROUND OF THE INVENTION

The present invention relates to a cap for use with a cannula and, more particularly, to a cap having a valve for resealably providing access to the interior of a cannula.

A prior art cannula is shown in FIG. 1 and includes a flexible body 10 having a flexible end 12 for insertion into a blood vessel. Prior to insertion of the cannula into the blood vessel, a needle 14 must be inserted through the cannula such that the pointed end of the needle extends beyond the flexible end 12. The needle allows the cannula to be guided through a patient's skin and to penetrate the blood vessel as the cannula 10 is inserted therein.

Subsequent to the insertion of the flexible end 12 into a blood vessel, the needle 14 is extracted in order to allow the insertion of a tube for allowing passage of blood or other fluids to r from the cannula 10 through the tube. In order to provide a proper seal around the needle and the tube inserted into the cannula and to prevent blood from flowing out of the cannula when the needle is extracted, a cap member 16 is provided positioned on the end of the cannula 10 and includes a plurality of slits extending radially across the center of the cap 16 for providing a recloseable opening for insertion of the needle and tube therethrough.

A recurring problem with the above-described arrangement is the prevention of small leaks through the slits in the cap member after the needle 14 has been withdrawn.

One prior art solution for properly sealing a cannula is shown in U.S. Pat. No. 4,655,752 issued to Honkanen et al in which a pair of seal members are provided for closing off the end of a cannula. In particular, a first seal member is provided having a conical shape and a cruciform slit for permitting passage of a surgical instrument therethrough. It is disclosed that fluid pressure will force the cruciform slit portion to contract together to form an impervious seal to fluid flow. However, such a construction depends on the seal members defining the slit being in proper alignment with each other in order to prevent fluid flow and therefore requires that the end portions of the seal be formed as a sufficiently stiff structure to prevent collapse of the seal members in toward each other. In order to prevent fluid flow past the first seal member when a tube is inserted therethrough, a second seal member lacking slits is required to sealingly contact the tube. Thus, two seals are required to effectively prevent flow through the valve portion of the cannula.

Accordingly, there is a need for a cap member having a valve portion which will reliably reseal the cannula end after removal of an instrument or tube therefrom. In addition, there is a need for a cap member which will provide an effective seal around the exterior of an instrument or tube which has been inserted into fluid communication with the interior of a cannula.

SUMMARY OF THE INVENTION

The present invention provides a cap for resealably sealing the end of a cannula to allow the insertion and removal of a tube or surgical instrument such as a needle into the cannula.

The cap includes a sleeve defining cylindrical inner and outer surfaces for the cap and a first flange extending radially inwardly from the inner surface of the sleeve at a first end of the cap. A valve body is formed integrally with a radially inner edge of the first flange and extends from the first cap end toward a second end of the cap in spaced relationship to the inner wall of the sleeve. The valve body defines an elongated tube-like member and includes an inlet end adjacent to the first cap end and an outlet end located intermediate the first and second cap ends.

The valve body is formed by four radially extending lip or gusset members which are spaced circumferentially from each other and define a right angled cross at an outlet end of the valve body located distal from the inlet end. Each of the lip members includes a pair of web members converging toward each other from the inlet end to the outlet end wherein the web members of each of the lip members meet along a radial line at the outlet end to form a resealable opening for allowing passage of a tube or medical instrument through the outlet end.

The web members of adjacent lips intersect each other along web intersection lines and each of the intersection lines extend radially inwardly in a direction from the inlet to the outlet end of the valve body.

cap further includes a second flange located at the second cap end and extending radially inwardly a lesser amount than the first flange. The second flange is configured to engage over a radially outwardly extending flange located on an end of a cannula. Thus, when the cap is placed over the end of a cannula the second flange and sleeve surround and form a seal with an exterior surface of the cannula and the valve body will extend into the interior of the cannula where the lip members form a normally closed opening preventing fluid flow out of the cannula through the cap. By providing converging webs forming the lip members, any pressure exerted by fluids in the cannula upon the lip members causes the web members to be compressed inwardly toward each other, thus firmly closing the valve to prevent fluid flow out of the cannula.

Other objects and advantages of the invention will be apparent from the following description, the accompanying drawings, and the appended claims.

DETAILED DESCRIPTION OF THE PREFERRED EMBODIMENT

Figure 1:
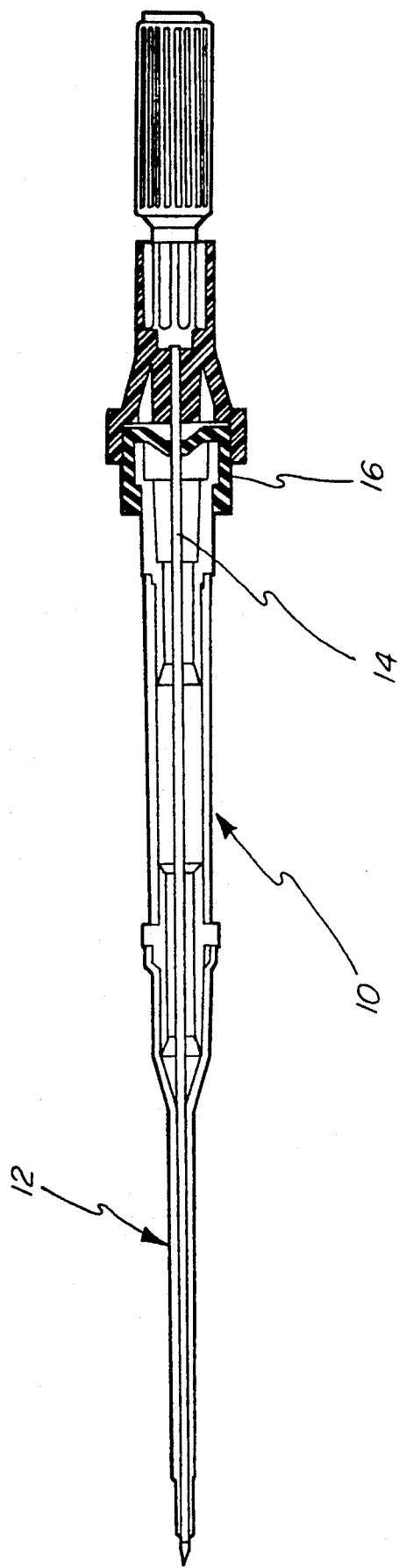
FIG. 1 is an elevational view in partial cross-section of a prior art cap member in place on a cannula.
Figure 2:
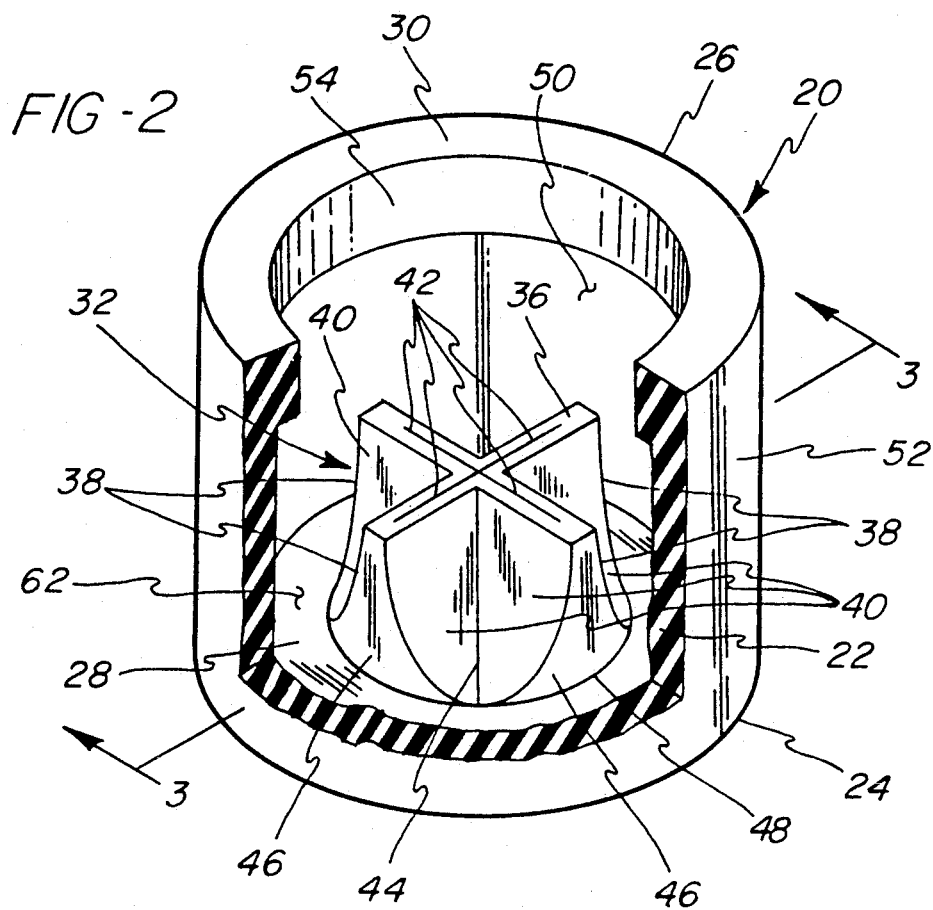
FIG. 2 is a partially cut away perspective view of the cap member of the present invention.

Referring to FIG. 2, the cap 20 of the present invention generally includes a sleeve member 22 defining a first end 24 and second end 26 of the cap 20. A first flange 28 is formed integrally with and extends radially inwardly from the sleeve 22 at the first end 24 of the cap 20, and a second flange 30 is formed integrally with the sleeve 22 and extends radially inwardly from the sleeve 22 at the second end 26 of the cap 20.

Figure 3:
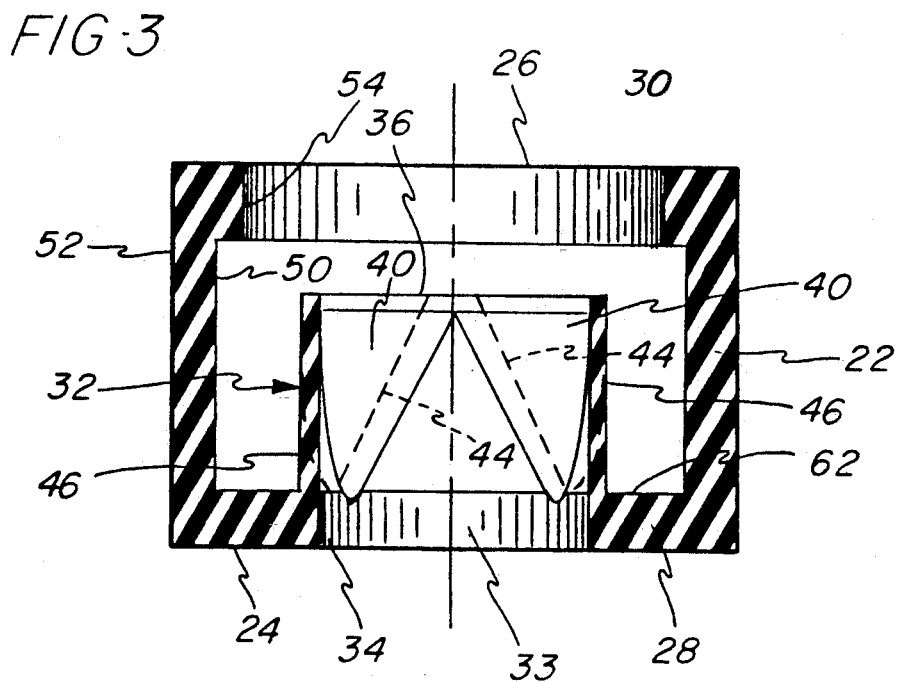
FIG. 3 is a cross-sectional view of the cap member of the present invention taken along line 3—3 in FIG. 2.

A valve body 32 is formed integrally with the first flange 28 and extends from the first end 24 toward the second end 26 of the sleeve member 22. As may be seen in FIG. 3, the valve body 32 includes an inlet end 34 located adjacent to the first sleeve end 24 and defined by a radially inner annular surface 33 of the flange 28, and an outlet end 36 located intermediate the first and second ends 24, 26 of the sleeve member 22.

The valve body 32 is formed as a tube-like member defining a fluid passage through the cap 20. As may be seen in FIGS. 2, 4 and 5, the valve body 32 includes lip members 38 which extend radially from the center of the valve body 32 and which are circumferentially spaced from each other. The lip members 38 are each defined by a pair of web members 40 wherein the web members 40 of each of the lip members 38 converge from the inlet end 34 toward the outlet end 36 to meet and form a normally closed slit opening 42 at the outlet end 36 of the valve body 32.

As is best shown in FIG. 2, the ends of the web members 40 define a substantially planar right angled cross-shaped surface at the outlet end of the valve body 32 and the slits 42 extend through the planar surface at the outlet end 36 and are configured to also form a right-angled cross at the outlet end 36.

Figure 4:
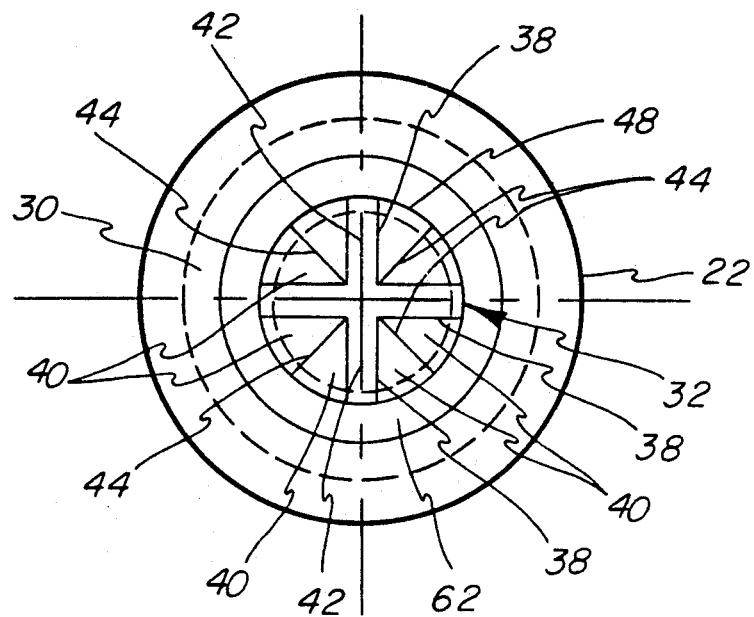
FIG. 4 is an end view taken from an outlet end of the cap.
Figure 5:
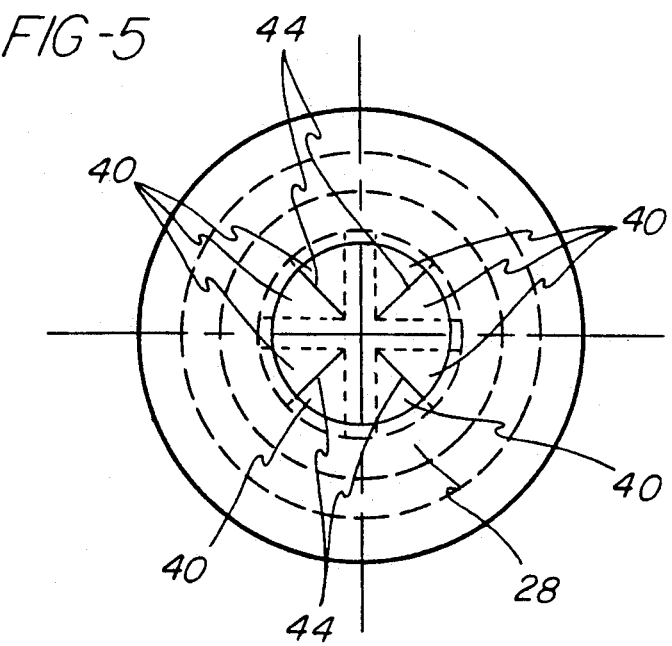
FIG. 5 is an end view taken from an inlet end of the cap.

As may be seen in FIGS. 4 and 5, the web members 40 of adjacent lip members 38 intersect to form intersection lines 44 between the lip members 38. Each of the intersection lines 44 extends radially inwardly in a direction from the inlet end 34 toward the outlet end 36 (see FIG. 3). In addition, each of the lip members 38 is provided with an outer wall 46 connecting its respective pair of web members 40 and defining an outer circumferential extent of the valve body 32, and at the intersection of the valve body 32 with the first flange 28 defines a circular intersection line 48.

It should be apparent that the configuration of the lip members 38 is such that the lip members 38 essentially form a configuration resembling a pair of intersecting duck bill valves such that increasing fluid pressure against the exterior of the web members 40 will cause the slit openings 42 to be firmly closed. When a needle or tube is inserted through the inlet end 34 it will contact the edges of the web members 40 defining the slit openings 42 to cause the outlet end 36 of the valve to open and allow passage of the needle or tube. It should be noted that the web members 40 are capable of providing a wide circumference opening whereby a tube having a circumference equal to the circumference of the surface 33 may be inserted without stretching, tearing or otherwise damaging the lip members 38. In other words, the web members 40 form flexible gusset portions creased along the intersection lines 44 which may move radially outwardly in response to passage of a tube through the valve, and subsequently return to their original closed positions upon removal of the tube.

The cap member is preferably formed from an elastomeric material such as medical grade silicon and, as may be seen in FIG. 2, the sleeve 22 is formed with substantially cylindrical inner and outer walls 50, 52, respectively for facilitating engagement and sealing with the end of a cannula. In addition, the second flange 30 extends a lesser radial extent inwardly than the first flange 28 and includes an inner cylindrical surface 54 which is also designed to engage and form a seal with an outer wall of a cannula.

Figure 6:
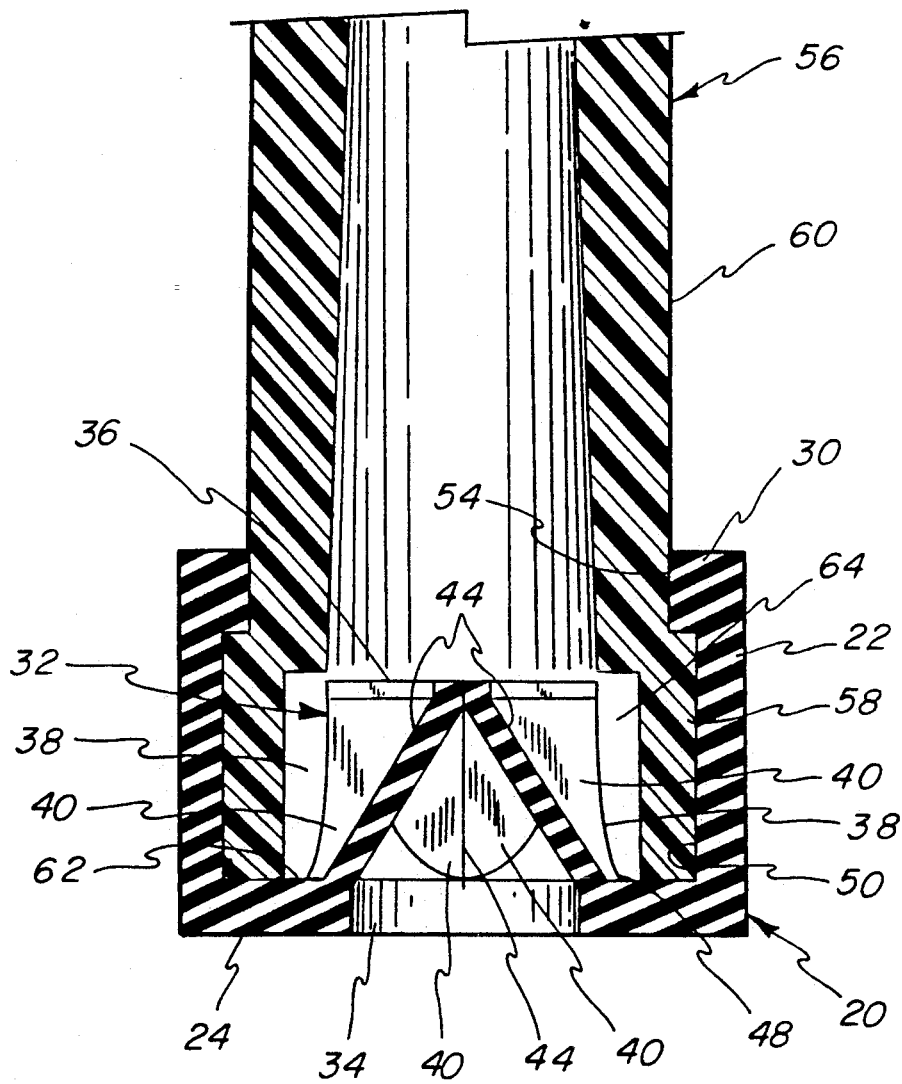
FIG. 6 is a cross-sectional view taken along a line of intersection between adjacent web members and showing the cap in place on the end of a cannula.

Referring to FIG. 6, the cap 20 of the present invention is shown in position on an end portion of a cannula 56. The cannula 56 includes a radially extending flange portion 58. The cap is positioned such that the inner wall of the sleeve 22 engages and forms a seal with an outer surface of the flange 58 and the inner surface 54 of the second flange 30 engages and forms a seal with an outer wall portion 60 of the cannula 56.

As a result of the intersection line 48 being spaced from the inner sleeve wall 50, the end of the cannula 56 may extend into engagement with an inner surface 62 of the first flange to complete the seal between the cannula 56 and the cap 20. With the cap 20 thus in position, the valve body 32 will extend into the cannula 56 with the lip members 38 in spaced relation to the cannula 56. The cannula 56 is preferably provided with an annular groove or indentation 64 adjacent to the lip members 38 such that a tube having a diameter substantialy equal to the interior diameter of the cannula 56 may be inserted and sufficient room will be provided for outward movement of the lip members 38 as the web members 40 move into the indentation 64.

It should also be noted that the circumference of the inner annular surface 33 is such that it will engage and form a seal with a tube inserted into the cannula 56. Thus, the cap 20 of the present invention provides two integrally formed seal portions wherein the web members 40 form an easily opened portion creating a seal when a tube is not passing through the valve, and opening to a large circumference in response to the passage of a tube through the valve. In addition, the inner surface 33 of the flange 28 forms a second seal about a tube inserted through the valve to prevent passage of fluids out of the cannula 56 when the lips 38 have been moved to an open position by the tube.

In addition, as a result of using converging web members 40 configured to resemble intersecting duckbill valve members, any reverse fluid flow in a direction from the outlet end 36 toward the inlet end 34 causes an additional closing biasing force to firmly seal the slit areas 42 and prevent fluid leakage through the cap 20 when a tube is not present in the valve.

Further, it should be noted that additional lip members 38 may be provided while remaining within the scope of the invention. For example, five or more radially extending lips may be provided, each of the lips including a slit formed by adjoining web members.

While the form of apparatus herein described constitutes a preferred embodiment of the invention, it is to be understood that the invention is not limited to this precise form of apparatus and that changes may be made therein without departing from the scope of the invention which is defined in the appended claims.

What is claimed is:

1. A cap for sealing a cannula comprising:
   a sleeve member including a first end and a second end and an interior wall between said first and second ends;
   an elongated valve body portion, said valve body portion having an inlet end and an outlet end;
   said inlet end of said valve body portion being located adjacent to said first end of said sleeve member;
   said valve body portion extending from said first end toward said second end of said sleeve member in spaced relation to said interior wall;
   said outlet end of said valve body portion including means defining intersecting slits for sealing said outlet end and allowing passage of a tube through said cap, and all of said slits define and lie in a common plane;

said outlet end of said valve body portion being located intermediate said first and second ends of said sleeve member; and said valve body portion and said sleeve defining a space therebetween for receiving and end of a cannula and for accommodating outward movement of said valve body portion.

2. The cap of claim 1 wherein said valve body portion includes substantially coplanar surfaces at said outlet end and said slits are defined in said coplanar surfaces.

3. The cap of claim 1 including a flange extending radially inwardly from said second end of said sleeve member such that said cap may be placed over the end of a cannula with said flange and said sleeve member surrounding and forming a seal with an exterior surface of the cannula and with said valve body portion extending into the cannula.

4. The cap of claim 1 wherein said valve body portion includes a plurality of radially extending lip members, said lip members each including a pair of web members wherein said web members of each of said lip members meet at said outlet end of said valve body portion to define said slits.

5. The cap of claim 4 including web intersection lines defined at each intersection of a web member of one of said lip members with a web member of an adjacent one of said lip members, each said intersection line extending radially inwardly from said inlet end to said outlet end.

6. The cap of claim 4 including four radially extending lip members wherein said lip members define a right angled cross at said outlet end.

7. The cap of claim 1 including a flange extending radially inwardly from said first end of said sleeve member, said valve body portion extending from an axially inner portion of said flange.

8. The cap of claim 7 wherein said flange includes a radially inner surface for forming a seal with a wall of a tube passing through said outlet end.

9. The cap of claim 1 wherein said valve body portion is a tube-like member forming a fluid passage through said cap.

10. The cap of claim 1 wherein said valve body is configured as two intersecting duckbill valves having slits intersecting to define a right angle cross at said outlet end.

11. A cap for sealing a cannula comprising:

s sleeve including a wall defining a cylindrical outer surface and first and second cap ends;

a first flange extending radially inwardly from said sleeve at said first cap end;

a second flange extending radially inwardly from said sleeve at said second cap end, said second flange extending inwardly a lesser amount than said first flange;

an inner cylindrical wall defined by said sleeve between said first and second flange;

a valve body formed integrally with a radially inner edge of said first flange and extending from said first cap end toward said second cap end in spaced relation to said inner cylindrical wall, said valve body defining an elongated tube-like member and including an inlet end adjacent to said first cap end and an outlet end located intermediate said first and second cap ends;

four radially extending lip members spaced circumferentially from each other and defining a right angled cross at said outlet end;

each of said lip members including a pair of web members converging toward each other from said inlet to said outlet end, said web members of each of said lip members meeting at said outlet end to form a resealable opening for allowing passage of a tube through said outlet end;

a web intersection line defined at each intersection of a web member of one of said lip members with a web member of an adjacent one of said lip members, each said intersection line extending radially inwardly from said inlet end to said outlet end; and wherein said cap is formed of an elastomeric material and may be placed on the end of a cannula with said second flange and said sleeve surrounding and forming a seal with an exterior surface of the cannula and with said valve body extending into the cannula, said lip members forming a normally closed opening preventing fluid flow out of the cannula through said cap, and said valve body and said sleeve defining a space therebetween for receiving the cannula and for accommodating outward movement of the lip members.

12. A cap for sealing a cannula comprising:

an elongated substantially cylindrical sleeve defining first and second cap ends;

a first flange extending radially inwardly from said first cap end;

an elongated tubular valve body extending from an inner edge of said first flange in spaced relation to said cylindrical sleeve;

a plurality of radially extending lips spaced circumferentially from each other, each said lip defined by a pair of webs; and wherein said tubular valve body and said sleeve define an annular space within said sleeve for receiving an annular end portion of a cannula and for accommodating movement of said lips laterally outwardly, wherein said first flange is formed integrally with said sleeve and said valve body.

13. The cap of claim 12 including a second flange extending radially inwardly from said second cap end wherein said first flange defines an inner sealing surface for sealingly engaging a tube passing through said valve body and said second flange defines a sealing surface for engaging an outer wall of the cannula sealed by said cap.

14. The cap of claim 12 in combination with a cannula having an end portion thereof in contact with said sleeve and located adjacent to said first flange wherein an annular space is defined between said valve body and said cannula for accommodating movement of said lips outwardly.

* * * * *